United States Patent [19]

Koenig et al.

[11] 4,039,554
[45] Aug. 2, 1977

[54] MANUFACTURE OF 4-METHYLOXAZOLE

[75] Inventors: Horst Koenig, Ludwigshafen; Walter Boell, Dannstadt-Schauernheim, both of Germany

[73] Assignee: BASF Aktiengesellschaft, Ludwigshafen, Germany

[21] Appl. No.: 623,039

[22] Filed: Oct. 16, 1975

[30] Foreign Application Priority Data

Oct. 31, 1974 Germany .............................. 2451725

[51] Int. Cl.$^2$ ........................................... C07D 263/04
[52] U.S. Cl. ............................................... 260/307 R
[58] Field of Search .................................... 260/307 R

[56] References Cited

U.S. PATENT DOCUMENTS 3,862,169  1/1975  Weberndörfer ................. 260/307 R Primary Examiner—Donald G. Daus
Assistant Examiner—Jose Tovar
Attorney, Agent, or Firm—Keil, Thompson & Shurtleff

[57] ABSTRACT

4-Methyloxazole is manufactured by reaction of formimido-esters with hydroxyacetone. 4-Methyloxazole, manufactured by the process of the invention, is a starting material for the manufacture of dyes, pharmaceuticals, pesticides and vitamins.

9 Claims, No Drawings

MANUFACTURE OF 4-METHYLOXAZOLE

The present invention relates to a process for the manufacture of 4-methyloxazole by reaction of formimido-esters with hydroxyacetone.

As is disclosed by Rodd, Chemistry of Carbon Compounds (Elsevier Co., N.Y., 1957), volume IVa, pages 353 – 357, oxazoles which are unsubstituted in the 2-position and are at the same time substituted by alkyl in the 4-position cannot be manufactured by conventional methods. This is true specifically of the methods using imido-esters or α-acyloxyketones as starting materials. It is necessary to choose reactions involving reactants which give oxazoles which are 2-substituted and/or are substitured in the 4-position by a reactive group such as carbalkoxy, if the cyclization, and a substantial yield of end product, are to be achieved. Unsubstituted oxazole itself was first manufactured by hydrolysis and decarboxylation of 4-carbethoxyoxazole (Chem. Rev., 61 (1961), 198).

A pulication in Angew. Chem., 83 (1971), 358, points out that oxazoles with hydrogen in the 2-position are difficult to obtain by conventional synthesis and recommends a method of entailing the reaction of α-metallized alkyl isocyanides with acylating agents. However, this method only gives 4,5-substituted oxazoles or 4-phenyloxazole.

The sole method of manufacturing 4-methyloxazole (see also Ann. Soc. Chim. Polonorum, 46 (1972), 1,679) is that disclosed by Cornforth, entailing the reaction of α-chloroacetoacetic acid ethyl ester with ammonium formate in formic acid, subsequent hydrolysis of the resulting oxazole ester with sodium hydroxide solution and decarboxylation of the 4-methyloxazole-5-carboxylic acid thus obtained. Direct methods of manufacture of this end product from the starting materials, without subsequent elimination of other substituents, have not previously been disclosed. As the method entails 3 steps, the reaction is involved, lengthy and unsatisfactory in respect of economy, simplicity of operation and yield of end product.

It is an object of the present invention to provide a process, using more easily accessibly starting materials, for producing 4-methyloxazole in better yield and purity more simply and more economically.

We have found that this object is achieved when formimido-esters of the formula

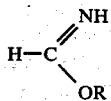   I wherein R is an aliphatic, cycloaliphatic, araliphatic or aromatic radical, are reacted with hydroxyacetone.

When formimido-methyl ester is used, the reaction may be presented by the following equation:

$H_3CO-CH=NH + HOCH_2COCH_3 \longrightarrow$

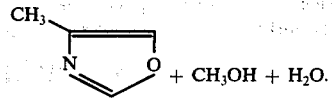 $+ CH_3OH + H_2O$.

Compared to the prior art, the process of the invention uses more easily accessible starting materials and gives 4-methyloxazole more simply and more economically and in better yield and purity. The reaction takes place in one step, at a higher reaction rate, and because of the simple method, which reduces personnel requirements and equipment costs, it is more reliable to operate, even continuously, and therefore more suitable for industrial operation. All these advantages are surprising in the light of the cited prior publications.

The starting material I can easily be manufactured by conventional methods (Houben-Weyl, Methoden der Organischen Chemie, volume 8, pages 697 – 701; Chem. Rev., loc.cit., pages 179 – 188), for example by the Pinner reaction, starting from hydrogen cyanide, an alcohol or phenol and an acid HX:

Further methods of manufacture are the reaction of formamide either with an acyl chloride and an alcohol or phenol (German Published Application No. 1,568,389):

or with a chloroformic acid ester (German Pat. No. 948,973):

The starting material I may be used as the free ester or, preferably, in the form of one of its salts as obtained from its process of manufacture, e.g. in the form of a salt with an inorganic acid, preferably a sulfate, hydrobromide or, in particular, hydrochloride. It may be reacted with hydroxyacetone in stoichiometric amount or in excess, preferably using from 1 to 3 moles of starting material I per mole of hydroxyacetone. Preferred starting materials I are those wherein R is alkyl of 1 to 12 carbon atoms, cycloalkyl of 5 to 10 carbon atoms, aralkyl of 7 to 12 carbon atoms or phenyl. As a rule, esters of primary or, preferably, of secondary, advantageously fairly high molecular weight, alcohols are used. The above radicals may further be substituted by groups which are inert under the reaction conditions, e.g. alkyl or alkoxy of 1 to 6 carbon atoms.

Thus, it is possible to use, as starting materials I, formimido-esters, especially in the form of their hydrochlorides, wherein R in

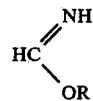

is isopropyl, sec.-butyl, isobutyl, 4-methyl-2-pentyl, 2-octyl, 2-ethyl-hexyl, diisobutylcarbinyl, cyclopentyl, phenyl, 2-methyl-cyclohexyl, 3-methyl-cyclohexyl, 4-methyl-cyclohexyl, 2-ethyl-cyclohexyl, 2,6-dimethyl-cyclohexyl, 4-tert.-butyl-cyclohexyl, 2-n-butoxy-ethyl, diisopropylcarbinyl, methyl, n-butyl, ethyl, n-propyl, benzyl, p-ethylphenyl, cyclohexyl, o-toluyl, phenylethyl, cycloheptyl or cyclooctyl.

As a rule, a basic compound is added when the salt of a formimido-ester I is reacted with hydroxyacetone. Preferably, the starting material I is reacted in the presence of at least the equivalent weight, preferably from 1 to 2 times the equivalent weight, and especially from 1.1 to 1.5 times the equivalent weight, based on starting material I, of a basic compound. Preferred basic compounds are primary, secondary and especially tertiary amines, alkaline earth metal compounds and especially alkali metal compounds as well as appropriate mixtures. Alkali metal compounds and alkaline earth metal compounds which may be used with advantage are the hydroxides, oxides, carbonates, bicarbonates, salts of weak or polybasic acids and alcoholates of calcium, barium, lithium and especially sodium and potassium. Specific examples of basic compounds which may be used are potassium hydroxide, sodium hydroxide, potassium carbonate, sodium carbonate, lithium carbonate, sodium bicarbonate, potassiium bicarbonate, calcium hydroxide, bariium oxide, calcium carbonate, sodium acetate,-propionate,-ethylene-glycolate,-methylate,-ethylate and tripropylene-glycolate, trimethylamine, triethylamine, pyridine, N,N-dimethylaniline, quinoline, N-methylpyrrolidone, tri-n-butylamine, N,N-diethylaniline, dimethylaminoethanol, N-ethylpiperidine, N-methylpyrrolidine, ethylamine, diethylamine, aniline, N-methylaniline, benzylamine, cyclohexylamine, di-tert.-butylamine and isopropylamine. Tertiary amines, especially N,N-dialkylanilines and quinoline, are preferred.

The reaction is as a rule carried out at from −20° to +160° C, preferably from 0° to 100° C, under reduced or superatmospheric pressure or preferably at atmospheric pressure, continuously or batchwise. The reaction may be carried out without solvents or in the presence of an organic solvent which is inert under the reaction conditions.

Examples of suitable solvents are aromatic hydrocarbons, e.g. toluene, ethylbenzene, o-, m- and p-xylene, isopropylbenzene and methylnaphthalene, halohydrocarbons, especially chlorohydrocarbons, e.g. tetrachloroethylene, amyl chloride, cyclohexyl chloride, dichloropropane, methylene chloride, dichlorobutane, chloroform, chloronaphthalene, dichloronaphthalene, carbon tetrachloride, tetrachloroethane, trichloroethane, trichloroethylene, pentachloroethane, trichlorofluoromethane, o-, m- and p-difluorobenzene, 1,2-dichloroethane, 1,1-dichloroethane, n-propyl chloride, 1,2-cis-dichloroethylene, chlorobenzene, fluorobenzene, bromobenzene, iodobenzene, o-, p- and m-dichlorobenzene, o-, p- and m-dibromobenzene, o-, m- and p-chlorotoluene, 1,2,4-trichlorobenzene and 1,10-dibromodecane, sulfoxides such as dimethyl sulfoxide, ethers, for example ethyl propyl ether, dimethyl glycol, methyl tert.-butyl ether, n-butyl ethyl ether, di-n-butyl ether, diisoamyl ether, diisopropyl ether, anisole, phenetole, cyclohexyl methyl ether, diethyl ether, dioxane, tetrahydrofuran and thioanisole, nitrohydrocarbons, such as nitromethane, nitroethane, nitrobenzene, o-, m- and p-chloronitrobenzene, and o-nitrotoluene, formamide, dimethylformamide, N-methylpyrrolidone and appropriate mixtures. The amount of solvent used in suitably from 200 to 10,000% by weight, preferably from 400 to 1,000% by weight, based on starting material I. The amines added as the base, or the hydroxy compounds which also serve for the preparation of the formimido-esters, may also be used as solvents. In a preferred embodiment, the same solvent as is used for the preparation of the formimido-ester is used.

The reaction may be carried out as follows: a mixture of the starting material I, or of its salt, and hydroxyacetone, if appropriate together with a basic compound and/or a solvent, is kept at the reaction temperature for from 0.1 to 2 hours. The end product is then isolated from the reaction mixture by conventional methods, e.g. by distillation, or by treating the mixture with aqueous sodium hydroxide solution and distilling the organic phase. The method can be varied widely; thus, e.g., hydroxyacetone and base may be added either simultaneously, e.g. as mixture, or successively, with or without solvent, to the formimido-ester, if appropriate dissolved or suspended in a solvent. The sequence of the addition is immaterial. In another embodiment, the formimido-ester is added a little at a time to the mixture of hydroxyacetone and base. Another advantageous method is to bring the reactants together at from 10° to 20° C, gradually heat the mixture to 60° − 80° C and then distil the resulting 4-methyloxazole from the reaction vessel at atmospheric pressure or under reduced pressure.

In a preferred embodiment, the manufacture of the formimido-ester and the reaction according to the invention are carried out as 2 steps in the same medium. Suitably, the mixture of hydrogen cyanide, the alcohol required to form the ester and the acid, advantageously hydrogen chloride, are kept at the above reaction temperature, preferably at from −10° to +30° C, for from 10 to 60 minutes, hydroxyacetone and the basic compound are then added and the reaction according to the invention is carried out in the above manner. In manufacturing the ester, it is advantageous to use from 1 to 1.1 moles of alcohol and from 1 to 1.1 equivalents of acid, based on 1 mole of hydrogen cyanide. This particularly economical and simple embodiment of the invention may be carried out at atmospheric pressure or under reduced pressure, continuously or batchwise.

4-Methyloxazole, which may be manufactured by the process of the invention, is a valuable starting material for the manufacture of dyes, pharmaceuticals, pesticides and vitamins. Regarding its uses, reference may be made to the publications cited and to Russian Chem. Rev., 38 (7), 540 − 546 (1969). Derivatives of vitamin $B_6$ and of its secondary products may be manufactured from the end product (German Published Application No. 2,143,989).

In the Examples which follow, parts are by weight and bear the same relation to parts by volume as the kilogram to the liter.

EXAMPLE 1 a. Preparation of the ester I: a mixture of 45 parts of formamide and 108 parts of benzyl alcohol is added in the course of 30 minutes to a solution of 141 parts of benzoyl chloride in 700 parts by volume of ester at from 10° to 15° C. The mixture is stirred for 2.5 hours at room temperature and is then filtered, and the filter residue is washed with ether and dried under reduced pressure. 132 parts (77% of theory) of formimido-benzyl ester hydrochloride are obtained.

b. Preparation of 4-methyloxazole: the hydrochloride obtained is added a little at a time to a solution of 29 parts of hydroxyacetone and 180 parts of N,N-diethylaniline at from 15° to 20° C. The mixture is then slowly heated to 90° C and the 4-methyloxazole formed is distilled at 20 mm Hg into a cooled receiver. Fractional distillation gives 14.5 parts (44% of theory) of 4-methyloxazole of boiling point 88° − 89° C.

EXAMPLE 2 a. Preparation of the ester I: 54 parts of hydrogen cyanide are added to a solution of 200 parts of cyclohexanol and 550 parts by volume of heptane at −10° C. 76 parts of hydrogen chloride are then passed into the mixture in the course of 1 hour and the temperature is kept at +20° C by cooling. After a further hour, the formimido-cyclohexyl ester hydrochloride which has crystallized out is filtered off, washed with heptane and dried at 50° C/1 mm Hg. 305 parts (93% of theory) of melting point 113° C are obtained.

b. Preparation of 4-methyloxazole: 32.7 parts of formimido-cyclohexyl ester hydrochloride are added, a little at a time, to a solution of 7.4 parts of hydroxyacetone and 45 parts of N,N-diethylaniline at 15° C. The mixture is slowly heated to 70° C and the 4-methyloxazole formed is distilled at 20 mm Hg into a cooled receiver. Yield 5 parts (60% of theory) of 4-methyloxazole of boiling point 88° – 89° C.

EXAMPLES 3 to 20

The formimido-ester hydrochlorides listed in the Table are reacted analogously to Example 2. They are prepared analogously to Example 2 (a).

TABLE

| Ex. | R in ROCH=NH . HCl | Parts of starting material I | Molar ratio of ester to hydroxy-acetone | Yield of 4-methyl-oxazole, % of theory |
|---|---|---|---|---|
| 3 | methyl | 9.55 | 2:1 | 24 |
| 4 | isopropyl | 12.5 | 2:1 | 44 |
| 5 | sec.-butyl | 14 | 2:1 | 24 |
| 6 | isobutyl | 14 | 2:1 | 11 |
| 7 | 4-methyl-2-pentyl | 17 | 2:1 | 46 |
| 8 | 2-octyl | 19.5 | 2:1 | 50 |
| 9 | 2-ethyl-hexyl | 19.5 | 2:1 | 21 |
| 10 | diisobutylcarbinyl | 21 | 2:1 | 40 |
| 11 | cyclopentyl | 15 | 2:1 | 31 |
| 12 | phenyl | 16 | 2:1 | 19 |
| 13 | 2-methyl-cyclohexyl | 18 | 2:1 | 56 |
| 14 | 3-methyl-cyclohexyl | 18 | 2:1 | 47 |
| 15 | 4-methyl-cyclohexyl | 18 | 2:1 | 58 |
| 16 | 2-ethyl-cyclohexyl | 19.5 | 2:1 | 49 |
| 17 | 2,6-dimethyl-cyclohexyl | 19.5 | 2:1 | 19 |
| 18 | 4-tert.-butyl-cyclohexyl | 22 | 2:1 | 60 |
| 19 | 2-n-butoxy-ethyl | 18.5 | 2:1 | 38 |
| 20 | diisopropylcarbinyl | 18 | 2:1 | 32 |

EXAMPLE 21 a. Preparation of the ester I: 16.4 parts of formimido-cyclohexyl ester hydrochloride are introduced, a little at a time, into a stirred mixture of 15.2 parts of potassium carbonate, 50 parts by volume of water and 75 parts by volume of methylene chloride, at +5° C. The organic phase is separated off and dried over sodium sulfate. After stripping off the solvent, 10.8 parts of formimido-cyclohexyl ester (85% of theory) remain.

b. Preparation of 4-methyloxazole: a mixture of 6.4 parts of formimido-cyclohexyl ester and 3.7 parts of hydroxy-acetone is heated to 150° C in the course of 30 minutes. At the same time the 4-methyloxazole formed is distilled off. 0.5 part of 4-methyloxazole of boiling point 88.5° C is obtained.

EXAMPLE 22

A mixture of 6.4 parts of formimido-cyclohexyl ester, 4.75 parts of chloroacetic acid and 3.7 parts of hydroxyacetone is heated at 60° C for 1 hour. At the same time the 4-methyloxazole formed is distilled at 20 mm Hg into a cooled receiver. After fractionation, 1.2 parts (27% of theory) of 4-methyloxazole of boiling point 88° C are obtained.

EXAMPLE 23

13.5 Parts of hydrogen cyanide are passed into a solution of 57 parts of 2-methylcyclohexanol in 135 parts by volume of methylene chloride at −10° C, and 20 parts of hydrogen chloride are then passed in at +20° C, whilst cooling. The mixture is stirred for 45 minutes at room temperature. Methylene chloride is then stripped off under reduced pressure until the residue is viscous but can still be stirred. 18.5 parts of hydroxyacetone and 91 parts of N,N-dimethylaniline are added at +10° C and the mixture is heated to 75° C. At the same time the 4-methyloxazole formed, and the residual methylene chloride, are distilled under reduced pressure into a cooled receiver. 15.8 parts (76% of theory) of 4-methyloxazole, of boiling point 88° C, are obtained after fractional distillation.

EXAMPLE 24

13.5 Parts of hydrogen cyanide are passed into a solution of 50.1 parts of cyclohexanol is 45 parts by volume of nitrobenzene at 0° C and 20 parts of hydrogen chloride are then passed in at +20° C, whilst cooling. The resulting suspension is stirred for 30 minutes at 20° C. 18.5 parts of hydroxyacetone in 91 parts of N,N-dimethylaniline are then added at +10° C and the mixture is heated to 75° C. At the same time the 4-methyl-oxazole formed is distilled at 20 mm Hg into a cooled receiver. 11.5 parts (55% of theory) of 4-methyloxazole, of boiling point 88° C, are obtained.

EXAMPLE 25

13.5 Parts of hydrogen cyanide are passed into a solution of 65 parts of 2-octanol in 45 parts by volume of o-dichlorobenzene at 0° C, and 20 parts of hydrogen chloride are then passed in at +20° C, whilst cooling. The viscous mixture is stirred for 30 minutes at 20° C. 18.5 parts of hydroxyacetone and 91 parts of N,N-dimethylaniline are then added at +10° C and the mixture is heated at 75° C for 1 hour. At the same temperature, 150 parts of 20% strength by weight aqueous sodium hydroxide solution are added, the mixture is cooled to room temperature, the organic phase is separated off and the 4-methyloxazole formed is distilled at atmospheric pressure (boiling point 88° C). Yield: 10.4 parts (50% theory).

EXAMPLE 26

The method used is analogous to Example, 23, with 139 parts of tri-n-butylamine in place of N,N-dimethylaniline. 8.3 parts (40% of theory) of 4-methyloxazole, of boiling point 88° C, are obtained.

EXAMPLES 27

The method used is analogous Example 2 (b), with 36.4 parts of N,N-dimethylaniline in place of N,N-diethylaniline. The yield of 4-methyloxazole is 5.2 parts (62% of theory), of boiling point 88° C.

EXAMPLE 28

The method used is analogous to Example 2 (b), with 38.7 parts of quinoline in place of N,N-diethylaniline. The yield of 4-methyloxazole is 4 parts (48% of theory), of boiling point 88° C.

EXAMPLE 29

16.4 Parts of formimido-cyclohexyl ester hydrochloride are introduced into a solution of 3.7 parts of hydroxyacetone, 14.9 parts of N,N-diethylaniline and 25 parts of N-methylpyrrolidone at −25° C. The mixture is then heated to 70° C and the 4-methyloxazole formed is distilled at 20 mm Hg into a cooled receiver. Yield, 4.7 parts (56% of theory), of boiling point 88° C.

We claim:

1. A process for the manufacture of 4-methyloxazole which comprises the step of: reacting a formimido-ester of the formula

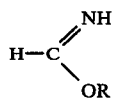   I wherein R is alkyl of 1 to 12 carbon atoms, cycloalkyl of 5 to 8 carbon atoms, aralkyl of 7 to 12 carbon atoms or phenyl, with hydroxyacetone at temperatures of from −20° to +160° C.

2. A process as claimed in claim 1, wherein the reaction is carried out with from 1 to 3 moles of starting material I per mole of hydroxyacetone.

3. A process as claimed in claim 1 wherein the reaction is carried out in the presence of at least 1 equivalent weight, based on starting material I, of a basic compound, wherein said basic compound is a primary, secondary and tertiary amine, or an alkaline earth or alkali metal compound of calcium, barium, lithium, sodium and potassium with hydroxides, oxides, carbonates, bicarbonates, salts of weak or polybasic acids and alcoholates.

4. A process as claimed in claim 1, wherein the reaction is carried out in the presence of from 1 to 2 equivalent weights, based on starting materials I, of a basic compound, wherein said basic compound is a primary, secondary and tertiary amine, or an alkaline earth or alkali metal compound of calcium, barium, lithium, sodium and potassium with hydroxides, oxides, carbonates, bicarbonates, salts of weak or polybasic acids and alcoholates 5. A process as claimed in claim 1, wherein the reaction is carried out at from 0° to 100° C.

6. A process as claimed in claim 1, wherein the reaction is carried out in the presence of from 200 to 10,000% by weight, based on starting material I, of an organic solvent which is inert under the reaction conditions.

7. A process as set forth in claim 1 wherein a salt of said ester is used as the starting material I.

8. A process as set forth in claim 7 wherein a sulfate, hydrobromide or hydrochloride of said ester is used as the starting material I.

9. A process as set forth in claim 8 wherein a hydrochloride of said ester is used as the starting material of I.

* * * * *